(12) United States Patent
Taeschler et al.

(10) Patent No.: US 11,332,456 B2
(45) Date of Patent: May 17, 2022

(54) METHOD FOR PREPARATION OF FLUORO ALKYLATED 1,4-DIOXENE BY HOMOGENEOUS NI CATALYSIS

(71) Applicant: Lonza Solutions AG, Visp (CH)

(72) Inventors: Christoph Taeschler, Visp (CH); Thomas Belser, Gils (CH); Stefan Ellinger, Visp (DE); Florencio Zaragoza Doerwald, Buochs (CH); Matthias Beller, Nienhagen (DE); Helfried Neumann, Rostock (DE); Florian Fischer, Rostock (DE); Shaoke Zhang, Rostock (DE)

(73) Assignee: Lonza Solutions AG, Visp (CH)

( * ) Notice: Subject to any disclaimer, the term of this patent is extended or adjusted under 35 U.S.C. 154(b) by 0 days.

(21) Appl. No.: 17/424,189

(22) PCT Filed: Feb. 20, 2020

(86) PCT No.: PCT/EP2020/054546
§ 371 (c)(1),
(2) Date: Jul. 20, 2021

(87) PCT Pub. No.: WO2020/169770
PCT Pub. Date: Aug. 27, 2020

(65) Prior Publication Data
US 2022/0041570 A1    Feb. 10, 2022

Related U.S. Application Data

(60) Provisional application No. 62/807,911, filed on Feb. 20, 2019.

(30) Foreign Application Priority Data

Feb. 20, 2019  (EP) ...................... 19158339
May 7, 2019   (EP) ...................... 19172869

(51) Int. Cl.
*C07D 319/12*   (2006.01)
*B01J 31/24*    (2006.01)

(52) U.S. Cl.
CPC ........ *C07D 319/12* (2013.01); *B01J 31/2495* (2013.01)

(58) Field of Classification Search
None
See application file for complete search history.

(56) References Cited

PUBLICATIONS

Hahn et al., "Synthesis of 5,6-Dihydro-2-trifluoromethyl-1,4-dioxin-3-carboxanilides through Polymer-bound Activated Ester: Construction of Dihydro-1,4-dioxin," Organic Chemistry Lab, Korea Institute of Science and Technology and Department of Chemistry, Kyonggi University, Jul.-Aug. 2000, pp. 1003-1008.

International Search Report and Written Opinion for PCT/EP2020/054546 dated Apr. 13, 2020, 12 pages.

Standley et al., "A Broadly Applicable Strategy for Entry into Homogeneous Nickel(0) Catalysts from Air-Stable Nickel(II) Complexes," Organometallics, Apr. 16, 2014, pp. 2012-2018.

*Primary Examiner* — Joseph R Kosack
(74) *Attorney, Agent, or Firm* — Dority & Manning, P.A.

(57) ABSTRACT

The invention discloses a method for the preparation of fluoro alkylated 1,4-dioxene by homogeneous Ni catalyzed fluoro alkylation with fluoro alkyl halides of 1,4-dioxane in the presence of a base.

9 Claims, No Drawings

METHOD FOR PREPARATION OF FLUORO ALKYLATED 1,4-DIOXENE BY HOMOGENEOUS NI CATALYSIS

CROSS REFERENCE TO RELATED APPLICATIONS

This application is the U.S. National Stage entry of International Application Number PCT/EP2020/054546 filed under the Patent Cooperation Treaty having a filing date of Feb. 20, 2020, which claims priority to U.S. Provisional Patent Application No. 62/807,911 having a filing date of Feb. 20, 2019, European Patent Application No. 19158339.2 having a filing date of Feb. 20, 2019, and European Patent Application No. 19172869.0 having a filing date of May 7, 2019, which are incorporated herein by reference.

TECHNICAL FIELD

The invention discloses a method for the preparation of fluoro alkylated 1,4-dioxene by homogeneous Ni catalyzed fluoro alkylation with fluoro alkyl halides of 1,4-dioxane in the presence of a base.

BACKGROUND OF THE INVENTION

I. Hanna in Tetrahedron Letters, 1999, 40, 2521-2524 discloses that furans are important functional groups that can be found in many natural products and have frequently been used as intermediates in organic synthesis, and report the synthesis of furans starting of 1,4-dioxene.

U.S. Pat. No. 3,592,825 discloses the preparation of 1,4-dioxene from a mixture of hydrogen, water and diethylene glycolover certain catalysts, and the use of p-dioxene as an intermediate in the preparation of polymers, for example, as viscosity improvers for motor oils, and in oxonation and epoxidation reactions to yield cyclic aldehydes and alcohols which are useful, for example, as plasticizers, surface active agents and adhesives.

Organofluorine chemistry plays an important role in medicinal, agricultural, and material sciences and fields. Fluoroalkyl groups have strong effects such as high stability and lipophilicity, in addition, longer fluoroalkyl groups have high water and oil resistance and low friction.

There was a need for a method for preparation of fluoro alkylated 1,4-dioxenes by direct C—H fluoro alkylation.

Unexpectedly a reaction with homogeneous Ni catalysis was found that meets these requirements, that uses as substrate 1,4-dioxane. No dialkylated products are observed.

ABBREVIATIONS

In this text, the following meanings are used, if not otherwise stated:
alkyl linear or branched alkyl, preferably linear;
DME 1,2-dimethoxyethane
1,4-dioxane CAS 123-91-1, compound of formula (1)

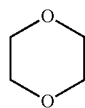

(1)

1,4-dioxene CAS 543-75-9, compound of formula (2)

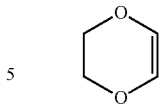

(2)

dppb 1,4-Bis(diphenylphosphino)butane, compound o formula (dppb)

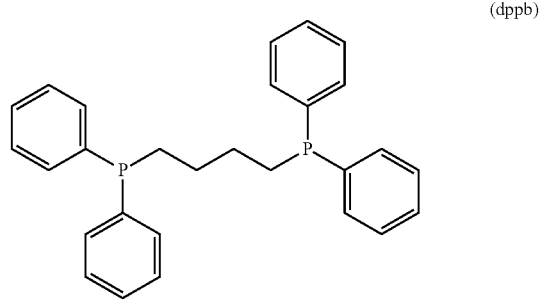 [SMILES: c1ccc(P(CCCCP(c2ccccc2)c2ccccc2)c2ccccc2)cc1]

(dppb)

dppf 1,1'-Bis(diphenylphosphino)ferrocen, compound of formula (4)

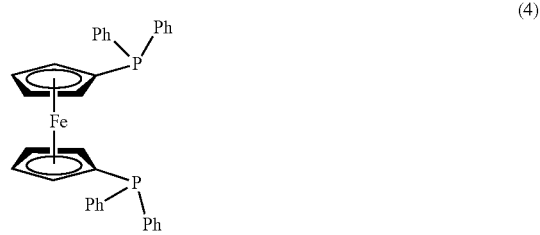

(4)

eq, equiv equivalent
halogen F, Cl, Br or I; preferably F, Cl or Br; more preferably F or Cl "linear" and "n-" are used synonymously with respect to the respective isomers of alkanes
MTBE methyl tert-butyl ether
Ni-cat2 (dppf)Ni(o-tol)Cl
PfP-H 1,1,1,2,3,3,3-heptafluoropropane
PhB-acid Phenylboronic acid, compound of formula (5)

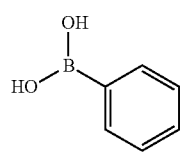

(5)

Ph₃P triphenylphosphine
PMHS polymethylhydrosiloxane
RT room temperature, it is used synonymously with the expression ambient temperature "wt %", "% by weight" and "weight-%" are used synonymously and mean percent by weight

SUMMARY OF THE INVENTION

Subject of the invention is a method for the preparation of a fluoro alkylated 1,4-dioxene by a reaction of 1,4-dioxane with a fluoro alkyl halide FAHALIDE by homogeneous catalysis using a Ni catalyst NICAT in the presence of a base BAS;
wherein
NICAT is Ni-cat1 or Ni-cat2;
Ni-cat1 is a combination of a nickel salt NISALT with a ligand LIG
NISALT is $NiCl_2$ or $Ni(NO_3)_2$;
LIG is selected from the group consisting of compound of formula (DPEPhos), compound of formula (dppb) and $Ph_3P$;

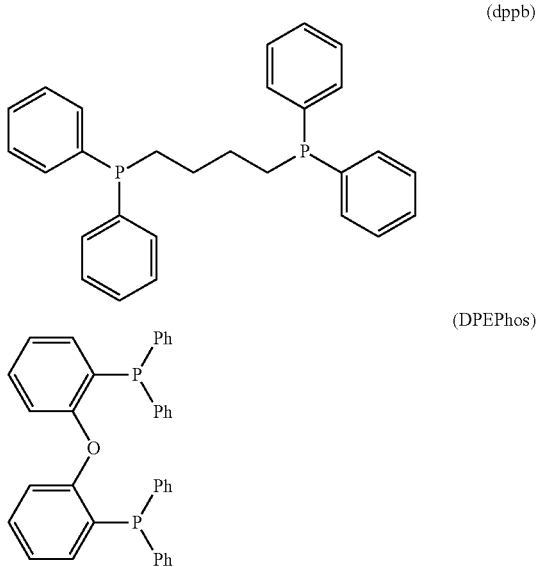

Ni-cat2 is compound of formula (Ni-cat2);

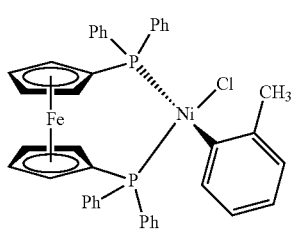

(Ni-cat2)

BAS is selected from the group consisting of $Cs_2CO_3$, $CsHCO_3$, $Na_2CO_3$, $K_3PO_4$, NaH and NaOtBu;
FAHALIDE is a compound of formula (FAHALIDE);

X2-R3-X1    (FAHALIDE)

R3 is $C_{1-20}$ alkylen, wherein in the alkylen chain at least one of the hydrogens is substituted by F;
X1 is Br or I;
X2 is Br or H.

DETAILED DESCRIPTION OF THE INVENTION

Preferably, when LIG is $Ph_3P$ then NISALT is $Ni(NO_3)_2$.
Preferably, when LIG is compound of formula (dppb) then NISALT is $NiCl_2$.
Preferably, $Ni(NO_3)_2$ is used in form of its hydrate $Ni(NO_3)_2$ $6H_2O$.

$NiCl_2$ can be used as such or as $NiCl_2(DME)$; $NiCl_2$ (DME) is a mixture of $NiCl_2$ and 1,2-dimethoxyethane in the molar ratio of 1:1;
preferably $NiCl_2$ is used as such.
Preferably, NISALT is $NiCl_2$ and LIG is compound of formula (dppb).
Preferably, BAS is selected from the group consisting of $Cs_2CO_3$, $Na_2CO_3$, $K_3PO_4$, NaH and NaOtBu;
more preferably, BAS is $Cs_2CO_3$, $Na_2CO_3$ or NaH.
Preferably, R3 is $C_{1-15}$ alkylen, wherein in the alkylen chain at least one of the hydrogens is substituted by F; more preferably, R3 is $C_{1-10}$ alkylen, wherein in the alkylen chain at least one of the hydrogens is substituted by F.
Especially, FAHALIDE is selected from the group consisting of perfluoro $C_{1-20}$ alkyl-X1, Br—$(CF_2)_{n3}$—Br, and $F_2HC$—X1;
more especially, FAHALIDE is selected from the group consisting of perfluoro $C_{1-15}$ alkyl-X1, Br—$(CF_2)_{n3}$—Br or $F_2HC$—X1;
even more especially, FAHALIDE is selected from the group consisting of perfluoro $C_{1-10}$ alkyl-X1, Br—$(CF_2)_{n3}$—Br or $F_2HC$—X1;
with n3 being an integer of 2 to 10;
preferably, n3 is 2, 3, 4, 5, 6;
more preferably, n3 is 2, 4 or 6;
even more preferably, n3 is 4.
In particular, FAHALIDE is selected from the group consisting of $F_{21}C_{10}$—I, $F_{21}C_{10}$—Br, $F_{17}C_8$—I, $F_{17}C_8$—Br, $F_{13}C_6$—I, $F_{13}C_6$—Br, $F_9C_4$—I, $F_9C_4$—Br, $F_7C_3$—I, $F_7C_3$—Br, $F_3C$—I, $F_3C$—Br, Br—$(CF_2)_4$—Br, $F_2HC$—I, and $F_2HC$—Br;
more in particular, FAHALIDE is selected from the group consisting of $F_{21}C_{10}$—I, $F_{17}C_8$—I, $F_{13}C_6$—I, $F_9C_4$—I, $F_7C_3$—I, and $F_3C$—I;
even more in particular, FAHALIDE is selected from the group consisting of $F_{21}C_{10}$—I, $F_{17}C_8$—I, $F_9C_4$—I, $F_7C_3$—I, and $F_3C$—I.
Especially, FAHALIDE is $F_{21}C_{10}$—I.
In one embodiment,
X1 is I;
X2 is H.
In one embodiment,
R3 is perfluoroalkylen.
In another embodiment,
R3 is perfluoro $C_{1-20}$ alkyl;
preferably, R3 is perfluoro $C_{1-15}$ alkyl;
more preferably, R3 is perfluoro $C_{1-10}$ alkyl.
Preferably, from 0.1 to 20 mol %, more preferably from 0.5 to 15 mol %, even more preferably from 1 to 10 mol %, especially from 2 to 7.5 mol %, more especially from 3 to 6 mol %, even more especially from 4 to 5.5 mol %, of NICAT are used in the reaction, the mol % are based on the molar amount of FAHALIDE.
Preferably, from 0.1 to 20 mol %, more preferably from 0.5 to 15 mol %, even more preferably from 1 to 12.5 mol %, especially from 2 to 10 mol %, more especially from 3 to 7.5 mol %, even more especially from 4 to 5.5 mol %, of LIG are used in the reaction, the mol % are based on the molar amount of FAHALIDE.
In case of FAHALIDE being in gaseous form at ambient temperature, then preferably FAHALIDE is used in the reaction in an amount which corresponds to a pressure of from 1 to 20 bar, more preferably from 1 to 15 bar, even more preferably from 1 to 10 bar, especially from 2 to 10 bar, more especially from 3 to 8 bar, even more especially from 4 to 8 bar, at ambient temperature.

Preferably, from 1 to 20 mol equivalents, more preferably 1 to 15 mol equivalents, even more preferably from 1 to 10 mol equivalents, especially from 1 to 7.5 mol equivalents, more especially from 1.5 to 5 mol equivalents, even more especially from 2 to 4 mol equivalents, of 1,4-dioxane are used in the reaction, the mol equivalents are based on the molar amount of FAHALIDE.

Preferably, from 0.1 to 10 mol equivalents, more preferably from 0.5 to 7.5 mol equivalents, even more preferably from 1 to 5 mol equivalents, especially from 1 to 4 mol equivalents, more especially from 1 to 3 mol equivalents, of BAS are used in the reaction, the mol equivalents are based on the molar amount of FAHALIDE.

The reaction temperature of the reaction is preferably from 20 to 200° C., more preferably from 50 to 175° C., even more preferably from 60 to 150° C., especially from 70 to 140° C.

The reaction time of the reaction is preferably from 1 to 96 h, more preferably from 5 to 72 h, even more preferably from 7.5 to 48 h, especially from 10 to 24 h, more especially from 12 to 20 h.

Preferably, the reaction is done under inert atmosphere. Preferably, the inert atmosphere is achieved by the use if an inert gas preferably selected from the group consisting of argon, another noble gas, lower boiling alkane, nitrogen, more preferably nitrogen.

The lower boiling alkane is preferably a $C_{1-3}$ alkane, i.e. methane, ethane or propane.

The reaction can be done in a closed system, it can be done at a pressure caused by the reaction mixture at the chosen temperature in a closed system. It is also possible to apply pressure with said inert gas. It is also possible to carry out the reaction at ambient pressure.

The reaction can be done in the presence of a an additive ADD;

ADD is selected from the group consisting of KI, norbornene, Zn, polymethylhydrosiloxane, and phenylboronic acid;

preferably, ADD is KI or norbornene.

Preferably, from 0.5 to 5 equivalents, more preferably from 0.75 to 3 equivalents, of ADD are used in the reaction, the equivalents are based on the molar amount of FAHALIDE.

The reaction can be done neat or in a solvent SOL, SOL is preferably selected from the group consisting of alkanes, chlorinated alkanes, ketones, ethers, esters, aliphatic nitrils, aliphatic amides, sulfoxides, $C_6F_6$, and mixtures thereof;

preferably SOL is selected from the group consisting of $C_{5-8}$ alkane, chlorinated $C_{5-8}$ alkane, acetone, methylethylketone, diethylketone, MTBE, tetrahydrofuran, methyltetrahydrofuran, ethylacetate, butylacetate, valeronitril, acetonitrile, dimethylformamide, dimethylacetamide, N-methylpyrrolidone, dimethylsulfoxide, $C_6F_6$, and mixtures thereof;

more preferably SOL is selected from the group consisting of acetone, methylethylketone, diethylketone, valeronitril, acetonitrile, dimethylsulfoxide, $C_6F_6$, and mixtures thereof;

even more preferably SOL is selected from the group consisting of acetone, methylethylketone, diethylketone, dimethylsulfoxide, $C_6F_6$, and mixtures thereof;

especially SOL is $C_6F_6$.

It is also possible to use 1,4-dioxane and/or FAHALIDE simultaneously as solvent, meaning that the reaction is done neat.

Preferably, the reaction is done neat or in $C_6F_6$ as SOL.

The amount of SOL is preferably from 0.1 to 100 fold, more preferably from 1 to 50 fold, even more preferably from 1 to 25 fold, especially from 1 to 12.5 fold, more especially from 1 to 10 fold, even more especially from 3 to 10 fold, of the weight of FAHALIDE.

After the reaction, the fluoro alkylated 1,4-dioxene can be isolated by standard methods such as evaporation of volatile components, extraction, washing, drying, concentration, crystallization, chromatography and any combination thereof, which are known per se to the person skilled in the art.

EXAMPLE

Abbreviations

Conv Conversion in mol % with regard to 1,4-dioxane
Sel Selectivity in mol % with regard to 1,4-dioxane
Ex Example
Proc (General) Procedure
T reaction temperature
t reaction time General Procedure 1: Ni-Salt A mixture of 1,4-dioxane, FAHALIDE, NICAT, LIG, BAS, ADD (all equivalents and amounts are specified in the experimental table) were placed in a thick-walled pressure tube (Ace pressure tube, Sigma-Adrich Art. Nr. Z564575). The gas atmosphere in the pressure tube was flushed with nitrogen, the tube was closed with a screw cap and heated (reaction temperature and reaction time are specified in Table 3). The resulting mixture was cooled to room temperature and diluted with dichloromethane (4 ml). The solids were removed by centrifugation (3000 rpm, 15 min). The obtained product solution was analyzed by quantitative GC analysis (internal standard hexadecane), $^{19}$F-NMR analysis using the internal standards 1,2-difluorobenzene or 1,4-difluorobenzene, or GC-MS. Isolation of the products was conducted by pipette column chromatography using FluoroFlash® reverse phase silica gel (Sigma Aldrich No.: 00866) and a gradient solvent elution (1. MeOH:H$_2$O (4:1. 10 mL) 2. MeOH (100%, 10 mL) 3. acetone (100%, 10 mL) for long chains perfluoroalkyl chains (alkyl chain containing 10 or more carbon atoms) or by normal phase silical gel chromatography using silicagel (Sigma Aldrich No.: 236802) and a gradient solvent elution (1. Pentane Ether (100%) 2. Pentane:Diethylether (50%:50%, 10 ml) for perfluoroalkyl chains containing less than 10 carbon atoms.

Procedure "Preformation of Ni-Cat2"

Preformation of Ni-cat2 was done according to Standley, E. A. et al., A Broadly Applicable Strategy for Entry into Homogeneous Nickel(0) Catalysts from Air-Stable Nickel (II) Complexes, Organometallics 2014, 33, 2012:

NiC$_2$.6H$_2$O (8.5 mmol, 2.02 g) and EtOH (25 mL) were placed in an argon flushed round bottom flask equipped with a septum and a reflux condenser (Schlenk-flask). Then dppf (8.5 mmol, 4.712 g) was added and the resulting reaction mixture refluxed for 30 min (temperature ca. 80° C.), before cooled to 0° C. for 10 min. The so formed solid was collected by filtration and washed twice with EtOH (2 times with 10 mL) and with diethylether (2 times with 10 mL). After drying of the solid under vacuum (ca. 20 mbar, room temperature) 4.98 g intermediate Ni-int1, (dppf)NiCl$_2$, corresponding to 85% yield was obtained as a deep green powder.

This Ni-int1 (6.81 mmol, 4.658 g) and 180 mL CH$_2$Cl$_2$ were placed in an argon flushed round bottom flask. The resulting solution was cooled to 0° C., then o-tolylmagnesium chloride (6.81 mmol, 0.945 M in THF, 7.21 mL) was added dropwise with vigorous stirring. Near the end of the addition, the color of the solution changed from green to orange. This solution was stirred for an additional 15 min at 0° C. after addition, then the solvent was evaporated under vacuum at room temperature. Then 25 ml MeOH were added and the reaction mixture was stirred for 5 min at room temperature. After cooling this mixture to 0° C., the solid was collected by filtration, the residue was washed with MeOH (2 times with 5 ml) and dried under vacuum (ca. 5 mbar) at room temperature to yield 4.63 g Ni-cat2, (dppf)Ni(o-tol)Cl, corresponding to 92% yield as a fine, bright yellow powder.

$^1$H NMR (400 MHz, CD2Cl2): delta=8.23-8.12 (m, 4H), 8.02-7.93 (m, 2H), 7.51-7.38 (m, 7H), 7.27 (td, J=8.3, 2.0 Hz, 2H), 7.21-7.15 (m, 1H), 6.99 (t, J=7.4 Hz, 1H), 6.76 (td, J=8.2, 2.6 Hz, 2H), 6.66-6.54 (t, 2H), 6.43 (t, J=7.4 Hz, 2H), 6.30 (t, J=6.8 Hz, 1H), 6.10 (d, J=7.1 Hz, 1H), 5.15 (s, 1H), 4.54 (m, 1H), 4.25 (s, 1H), 4.19 (s, 1H), 4.02 (d, J=10.1 Hz, 2H), 3.52 (m, 1H), 3.33 (m, 1H), 2.44 (s, 3H).

$^{31}$P NMR (162 MHz, CD$_2$Cl$_2$): delta=29.51 (d, J=25.9 Hz, 1P), 12.12 (d, J=25.9 Hz, 1P).

General Procedure 2: Fluoroalkylation Using Preformed Ni-Cat2

A mixture of FAHALIDE (1 eq, 0.2 mmol), Ni-cat2 (5 mol %, 0.01 mmol, 7.40 mg, prepared according to the procedure "Preformation of Ni-cat2"), 1,4-dioxane (10 eq, 2 mmol,) and BAS were placed in a thick-walled Ace pressure tube (Sigma-Aldrich Art. Nr. Z564575). The gas atmosphere in the pressure tube was flushed with nitrogen, the tube was closed with a screw cap and heated for the reaction time and at the reaction temperature specified in the tables. The resulting reaction mixture was cooled to room temperature and diluted with dichloromethane (4 ml). The solids were removed by centrifugation (3000 rpm, 15 min). The obtained product solution was analyzed by quantitative $^{19}$F-NMR analysis using 1,4-difluorobenzene or 1,2-difluorobenzene as internal standard, quantitative GC analysis using hexadecane as internal standard, or GC-MS.

Isolation of the products was conducted by pipette column chromatography using FluoroFlash® reverse phase silica gel (Sigma Aldrich No.: 00866) and a gradient solvent elution (1. MeOH:H$_2$O (4:1. 10 mL) 2. MeOH (100%, 10 mL) 3. acetone (100%, 10 mL) for long chains perfluoroalkyl chains (alkyl chain containing 10 or more carbon atoms) or by normal phase silical gel chromatography using silicagel (Sigma Aldrich No.: 236802) and a gradient solvent elution (1. Pentane Ether (100%) 2. Pentane:Diethylether (50%:50%, 10 ml) for perfluoroalkyl chains containing less than 10 carbon atoms.

Details of the examples are given in Tables 1, 2 and 3.

TABLE 1

| Ex | Proc | Substrate | FAHALIDE | Product |
|---|---|---|---|---|
| 1 | 2 | 1,4-dioxane | $C_{10}F_{21}I$ | 2-($C_{10}F_{21}$)-1,4-dioxene |
| 2 | 2 | 1,4-dioxane | $C_{10}F_{21}I$ | 2-($C_{10}F_{21}$)-1,4-dioxene |
| 3 | 2 | 1,4-dioxane | $C_{10}F_{21}I$ | 2-($C_{10}F_{21}$)-1,4-dioxene |
| 4 | 1 | 1,4-dioxane | $C_{10}F_{21}I$ | 2-($C_{10}F_{21}$)-1,4-dioxene |
| 5 | 1 | 1,4-dioxane | $C_{10}F_{21}I$ | 2-($C_{10}F_{21}$)-1,4-dioxene |
| 6 | 2 | 1,4-dioxane | $C_{10}F_{21}I$ | 2-($C_{10}F_{21}$)-1,4-dioxene |

TABLE 2

| Ex | Proc | Substrate Amount | FAHALIDE Amount | NICAT | LIG | ADD | BAS |
|---|---|---|---|---|---|---|---|
| 1 | 2 | 0.5 ml 0.5 g 2.8 eq | 0.2 mmol 130 mg 1 eq | Ni-cat2 5 mol % | — | — | Cs$_2$CO$_3$ 2 eq |
| 2 | 2 | 0.5 ml 0.5 g 2.8 eq | 0.2 mmol 130 mg 1 eq | Ni-cat2 5 mol % | — | — | NaH 2 eq |
| 3 | 2 | 0.5 ml 0.5 g 2.8 eq | 0.2 mmol 130 mg 1 eq | Ni-cat2 5 mol % | — | — | Na$_2$CO$_3$ 2 eq |
| 4 | 1 | 0.5 ml 0.5 g 2.8 eq | 0.2 mmol 130 mg 1 eq | NiCl2 5 mol % | dppb 5 mol % | — | Na$_2$CO$_3$ 2 eq |
| 5 | 1 | 0.5 ml 0.5 g 2.8 eq | 0.2 mmol 130 mg 1 eq | NiCl2 10 mol % | dppb 10 mol % | KI 1 eq | Na$_2$CO$_3$ 2 eq |
| 6 | 2 | 0.5 ml 0.5 g 2.8 eq | 0.2 mmol 130 mg 1 eq | Ni-cat2 5 mol % | — | norbornene 2 eq | Na$_2$CO$_3$ 2 eq |

TABLE 3

| Ex | Proc | Solvent | T | t | Conv | Sel | Yield | Remarks |
|---|---|---|---|---|---|---|---|---|
| 1 | 2 | neat | 120° C. | 16 h | 100% | 23% | 23% | $^{19}$F—NMR |
| 2 | 2 | neat | 120° C. | 16 h | 100% | 29% | 29% | $^{19}$F—NMR |
| 3 | 2 | neat | 80° C. | 16 h | 100% | 25% | 25% | $^{19}$F—NMR |
| 4 | 1 | neat | 80° C. | 16 h | 82% | 23% | 19% | $^{19}$F—NMR |
| 5 | 1 | neat | 80° C. | 16 h | 100% | 21% | 21% | $^{19}$F—NMR |
| 6 | 2 | neat | 80° C. | 8 h | 100% | 31% | 31% | $^{19}$F—NMR |

The invention claimed is:

1. A method for the preparation of a fluoro alkylated 1,4-dioxene by a reaction of 1,4-dioxane with a fluoro alkyl halide FAHALIDE by homogeneous catalysis using a Ni catalyst NICAT in the presence of a base BAS;

wherein

NICAT is Ni-cat1 or Ni-cat2;
- Ni-cat1 is a combination of a nickel salt NISALT with a ligand LIG
  - NISALT is $NiCl_2$ or $Ni(NO_3)_2$;
  - LIG is selected from the group consisting of compound of formula (DPEPhos), compound of formula (dppb) and $Ph_3P$;

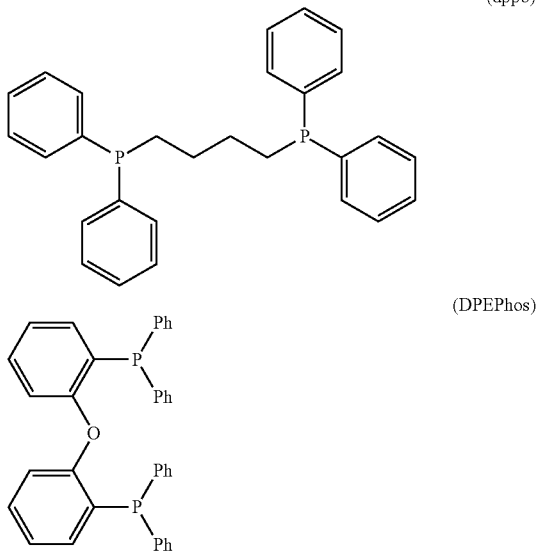

(dppb)

(DPEPhos)

Ni-cat2 is compound of formula (Ni-cat2);

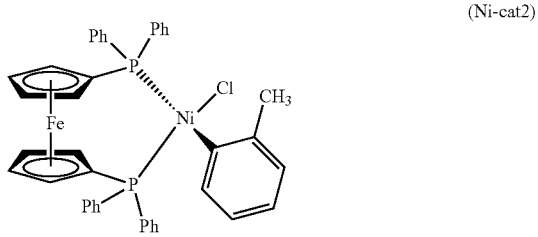

(Ni-cat2)

BAS is selected from the group consisting of $Cs_2CO_3$, $CsHCO_3$, $Na_2CO_3$, $K_3PO_4$, NaH and NaOtBu;

FAHALIDE is a compound of formula (FAHALIDE);

$$X2\text{-}R3\text{-}X1 \qquad \text{(FAHALIDE)}$$

R3 is $C_{1\text{-}20}$ alkylen, wherein in the alkylen chain at least one of the hydrogens is substituted by F;

X1 is Br or I;

X2 is Br or H.

2. The method according to claim 1, wherein

NISALT is $NiCl_2$ and LIG is compound of formula (dppb).

3. The method according to claim 1, wherein

BAS is selected from the group consisting of $Cs_2CO_3$, $Na_2CO_3$, $K_3PO_4$, NaH and NaOtBu.

4. The method according to claim 1, wherein

FAHALIDE is selected from the group consisting of perfluoro $C_{1\text{-}20}$ alkyl-X1, Br—$(CF_2)_{n3}$—Br, and $F_2HC$—X1;

with n3 being an integer of 2 to 10.

5. The method according to claim 1, wherein n3 is 2, 3, 4, 5, 6.

6. The method according to claim 1, wherein

FAHALIDE is selected from the group consisting of $F_{21}C_{10}$—I, $F_{21}C_{10}$—Br, $F_{17}C_8$—I, $F_{17}C_8$—Br, $F_{13}C_6$—I, $F_{13}C_6$—Br, $F_9C_4$—I, $F_9C_4$—Br, $F_7C_3$—I, $F_7C_3$—Br, $F_3C$—I, $F_3C$—Br, Br—$(CF_2)_4$—Br, $F_2HC$—I, and $F_2HC$—Br.

7. The method according to claim 1, wherein

FAHALIDE is selected from the group consisting of $F_{21}C_{10}$—I, $F_{17}C_8$—I, $F_{13}C_6$—I, $F_9C_4$—I, $F_7C_3$—I, and $F_3C$—I.

8. The method according to claim 1, wherein the reaction is done neat or in a solvent SOL.

9. The method according to claim 8, wherein SOL is selected from the group consisting of alkanes, chlorinated alkanes, ketones, ethers, esters, aliphatic nitrils, aliphatic amides, sulfoxides, $C_6F_6$, and mixtures thereof.

* * * * *